(12) United States Patent
Kim et al.

(10) Patent No.: US 11,266,678 B2
(45) Date of Patent: *Mar. 8, 2022

(54) COMPOSITION FOR ARTICULAR CAVITY INJECTION COMPRISING NUCLEIC ACID AND CHITOSAN

(71) Applicant: PharmaResearch Co., Ltd., Gangneung-si (KR)

(72) Inventors: Ik Soo Kim, Seongnam-si (KR); Han Gyu Kim, Wonju-si (KR); Su Yeon Lee, Seongnam-si (KR)

(73) Assignee: PHARMARESEARCH CO., LTD., Gangneung-si (KR)

( * ) Notice: Subject to any disclaimer, the term of this patent is extended or adjusted under 35 U.S.C. 154(b) by 222 days.

This patent is subject to a terminal disclaimer.

(21) Appl. No.: 16/327,472

(22) PCT Filed: Dec. 29, 2016

(86) PCT No.: PCT/KR2016/015507
§ 371 (c)(1),
(2) Date: Feb. 22, 2019

(87) PCT Pub. No.: WO2018/038331
PCT Pub. Date: Mar. 1, 2018

(65) Prior Publication Data
US 2019/0175638 A1 Jun. 13, 2019

(30) Foreign Application Priority Data
Aug. 25, 2016 (KR) .................. 10-2016-0108582
Dec. 26, 2016 (KR) .................. 10-2016-0179457

(51) Int. Cl.
| | | |
|---|---|---|
| *A61K 31/711* | (2006.01) | |
| *A61K 31/722* | (2006.01) | |
| *A61K 9/00* | (2006.01) | |
| *A61K 47/36* | (2006.01) | |
| *A61K 9/06* | (2006.01) | |
| *A61P 19/02* | (2006.01) | |
| *A61K 47/40* | (2006.01) | |
| *A61K 48/00* | (2006.01) | |

(52) U.S. Cl.
CPC .......... *A61K 31/711* (2013.01); *A61K 9/0019* (2013.01); *A61K 9/06* (2013.01); *A61K 31/722* (2013.01); *A61K 47/36* (2013.01); *A61K 47/40* (2013.01); *A61K 48/00* (2013.01); *A61P 19/02* (2018.01)

(58) Field of Classification Search
CPC .... A61K 31/711; A61K 31/722; A61K 47/36; A61K 9/0019; A61K 48/00; A61K 9/06; A61P 19/02
See application file for complete search history.

(56) References Cited

U.S. PATENT DOCUMENTS

| | | | |
|---|---|---|---|
| 2010/0184720 A1 | 7/2010 | Gavard Molliard et al. | |
| 2011/0059162 A1 | 3/2011 | Reed et al. | |
| 2014/0287061 A1* | 9/2014 | Landolina ........... | A61L 26/0014 424/617 |
| 2017/0326275 A1* | 11/2017 | Lecler ................. | A61K 9/08 |
| 2019/0054015 A1* | 2/2019 | Kim ..................... | C08L 5/00 |

FOREIGN PATENT DOCUMENTS

| | | | | |
|---|---|---|---|---|
| CN | 104546691 A | | 4/2015 | |
| FR | WO 2016/091778 | * | 6/2016 | ............... A61K 9/00 |
| IT | 2745849 | * | 6/2021 | ............ A61K 48/00 |
| JP | 2010-531863 A | | 9/2010 | |
| KR | 20-2009-0011604 A | | 11/2009 | |
| WO | 98/17321 A1 | | 4/1998 | |
| WO | 2013/070010 A1 | | 5/2013 | |

OTHER PUBLICATIONS

Lu et al. (International Journal of Pharmaceutics; 420 (2011) 358-365) (Year: 2011).*
Lu et al., "Novel hyaluronic acid-chitosan nanoparticles as non-viral gene delivery vectors targeting osteoarthritis", International Journal of Pharmaceutics, 420, (2011) 358-365.
European Search Report issued in European Patent Application No. 16914310.4 dated Mar. 31, 2020, 8 pages.
International Search Report issued for International Application No. PCT/KR2016/015507 dated May 22, 2017, 6 pages.
Lu H. et al., "Chitosan-Graft-Polyethylenimine/DNA Nanoparticles as Novel Non-Viral Gene Delivery Vectors Targeting Osteoarthritis", PLoS ONE, Jan. 2014, vol. 9, Issue 1, 12 pages.
Oliveira A. V. et al., "Combining Hyaluronic Acid with Chitosan Enhances Gene Delivery", Journal of Nanomaterials, vol. 2014, 1-9 pages.
Zhang X. et al., "Direct chitosan-mediated gene delivery to the rabbit knee joints in vitro and in vivo", Biochemical and Biophysical Research Communications, vol. 341, (2006) pp. 202-208.

(Continued)

*Primary Examiner* — Anna R Falkowitz
(74) *Attorney, Agent, or Firm* — Rothwell, Figg, Ernst & Manbeck, P.C.

(57) ABSTRACT

The present invention relates to a composition for articular cavity injection comprising a nucleic acid and chitosan. More specifically, in the present invention, it was confirmed that the sol-gel transition occurred depending on the temperature in the composition for articular cavity injection prepared through the mixing of the nucleic acid and chitosan, the proteoglycan biosynthesis of the cartilage tissue was increased by the injection of the composition and the cartilage regeneration effect was exhibited, and the pain was alleviated and the walking speed and stride which are the joint motilities were improved. Therefore, development of a therapeutic agent for arthritis having an excellent therapeutic effect using the composition for articular cavity injection comprising the nucleic acid and chitosan of the present invention is expected.

19 Claims, 4 Drawing Sheets

(56) References Cited

OTHER PUBLICATIONS

Lin Q. K. et al., "Hyaluronic acid and chitosan-DNA complex multilayered thin film as surface-mediated nonviral gene delivery system", Colloids and Surfaces B: Biointerfaces, 74 (2009) 298-303.
Fernandes J. C. et al., "Bone-protective Effects of Nonviral Gene Therapy With Folate-Chitosan DNA Nanoparticle Containing Interleukin-1 Receptor Antagonist Gene in Rats With Adjuvant-induced Arthritis", Molecular Therapy, vol. 16, No. 7, pp. 1243-1251, Jul. 2008.
Ruel-Gariepy and Leroux, "In situ-forming hydrogels-review of temperature-sensitive systems" European Journal of Pharmaceutics and Biopharmaceutics, 2004, 58: 409-426.
Lee et al., "DNA nanogels composed of chitosan and Pluronic with thermo-sensitive and photo-crosslinking properties" International Journal of Pharmaceutics, 2009, vol. 373: 93-99.
Zhou et al. Effect of molecular weight and degree of chitosan deacetylation on the preparation and characteristics of chitosan thermosensitive hydrogel as a delivery system, Carbohydrate Polymers, 2008, 73: 265-273.

\* cited by examiner

COMPOSITION FOR ARTICULAR CAVITY INJECTION COMPRISING NUCLEIC ACID AND CHITOSAN

CROSS-REFERENCE TO RELATED APPLICATIONS

The application is a 35 U.S.C. § 371 National Phase Entry Application from PCT/KR2016/015507, filed on Dec. 29, 2016, which claims the benefit of Korean Patent Application No. 10-2016-0108582 filed on Aug. 25, 2016, and Korean Patent Application No. 10-2016-0179457 filed on Dec. 26, 2016, the disclosures of which are incorporated herein in their entirety by reference.

TECHNICAL FIELD

The present invention relates to a composition containing a nucleic acid and chitosan for intra-articular injection.

BACKGROUND ART

An articulation is a place where a bone and another bone meet, and a thin layer of glass cartilage called articular cartilage is placed on facing faces of two bones constituting the articulation. The periphery of an articulation is covered with a connective tissue membrane in a form of a continuous periosteum, and thus called a joint capsule, and the lumen of the joint capsule is called an articular cavity. A thin membrane called the synovial membrane is on an inner surface of the articular cavity, and a small amount of synovial fluid is constantly released into the articular cavity to soften articular movements.

Articular diseases occur when problems arise in such an articulation, and of the articular diseases, the most prevalent disease is osteoarthritis. Osteoarthritis mainly invades fingers, knees, hip joints, and the lumbar spine, and pain and restricted movement are representative common symptoms although such symptoms slightly vary depending on the articulation invaded by osteoarthritis. Osteoarthritis therapy aims at the minimization of disability by mitigating pains and improving and maintaining articular movement (Lee Choong-Ki, 2000).

Osteoarthritis is a chronic disease, and requires long-term treatment due to the increased life expectancy. The choice of therapy is largely divided into non-pharmacological conservative treatment, pharmacotherapy, and surgical treatment, and therapeutic regimen should be established separately according to the severity and duration of symptom, radiologic finding, and age and accompanying disease, lifestyle, socioeconomic level, pre-onset activity, and the like of a patient. (Lee S. C., et al., 2010; and Yoon J. P., et al., 2012).

Unlike other articulation diseases, osteoarthritis is a disease that allows the intra-articular administration of drugs. Hyaluronic acid (HA), which is a polysaccharide, is one of the important components of articular synovial fluid. The presence of hyaluronic acid contributes to viscoelasticity of synovial fluid, allowing synovial fluid to act as a lubricant and shock absorber (Balazs E. A., et al., 1993). In addition, hyaluronic acid having a high molecular weight has an anti-inflammatory action and a pain killing action on inflammatory articulations (Kikuchi T., et al., 1996; Yoshimi T., et al., 1994; Sakakibara Y., et al., 1994). Therefore, the intra-articular administration of hyaluronic acid has been currently approved and used in several countries for the treatment of osteoarthritis.

The intra-articular administration of drug has advantages of attaining proper drug concentrations even at low doses and minimizing systemic side effects. However, the drugs administered into synovial fluid retain for a very short time, and thus the development of sustained-release formulations capable of sustained drug release in articulations is required (Gerwin N., et al., 2006).

Therefore, the present inventors verified an articular cavity pain mitigation effect and a cartilage regeneration effect by injecting a composition containing a nucleic acid and chitosan while studying a composition for intra-articular injection, and thus could complete the present invention.

Japanese Patent Publication No. 2010-531863 as a prior art discloses a gel type preparation for intra-articular injection, the preparation containing hyaluronic acid and at least one kind of another polysaccharide derived from nature. Therefore, said prior art has similar constituents to the present invention, but does not disclose a nucleic acid. In addition, Chinese Patent Publication No. 104546691 discloses a thermo-sensitive in-situ gel composition for intra-articular injection, the gel composition containing chitosan. Therefore, said prior art has similar constitutions to the present invention, but is different from the present invention in that said prior art does not disclose a nucleic acid. Korean Utility Publication No. 20-2009-0011604 discloses an intra-articular injection containing hyaluronic acid, but is different from the present invention in that said prior art does not disclose a nucleic acid and chitosan.

DETAILED DESCRIPTION OF THE INVENTION

Technical Problem

An aspect of the present invention is to provide a composition containing a nucleic acid and chitosan for intra-articular injection.

Furthermore, an aspect of the present invention is to provide a method for preparing a composition containing a nucleic acid and chitosan for intra-articular injection.

Technical Solution

The present invention is directed to a composition for intra-articular injection, the composition containing a nucleic acid and chitosan.

The content of the nucleic acid may be 0.1-3 wt % relative to a total weight of the composition.

The content of the chitosan may be 0.001-0.1 wt % relative to a total weight of the composition.

The weight ratio of the nucleic acid and the chitosan may be 1:1 to 3000:1.

The nucleic acid may be deoxyribonucleic acid (DNA), ribonucleic acid (RNA), or a mixture thereof. Preferably, the nucleic acid may be deoxyribonucleic acid (DNA).

The deoxyribonucleic acid may be selected from oligonucleotides, polynucleotides, and polydeoxyribonucleotides.

The nucleic acid may have a molecular weight of 1-100,000 kDa. The nucleic acid may have a molecular weight of preferably 10-10,000 kDa, and more preferably 50-3,500 kDa.

The chitosan may have a molecular weight of 3-1,000 kDa.

The composition may contain a water-soluble polymer as an additional ingredient.

The water-soluble polymer may be at least one selected from the group consisting of hyaluronic acid, chondroitin sulfate, glycogen, dextrin, dextran, dextran sulfate, hydroxypropyl methylcellulose, alginic acid, chitin, pullulan, collagen, gelatin, hydrolysates of all of the above, polyvinyl alcohol, polyvinylpyrrolidone, polyacrylic acid, and carboxyvinyl polymers. Preferably, the water-soluble polymer may be hyaluronic acid.

The composition may be a hydrogel, of which a sol-gel transition occurs depending on the temperature.

The intra-articular injection may be an administration for at least one symptom selected from the group consisting of herniated nucleus pulposus, frozen shoulder, impingement syndrome, carpal tunnel syndrome, degenerative arthritis, tennis/golf elbow, complex regional pain syndrome, other tendinitis symptoms, and chronic articular rheumatism.

Hereinafter, the present invention will be described in detail.

The composition containing a nucleic acid and chitosan for intra-articular injection may be prepared by comprising steps of i) placing a nucleic acid in a buffer solution and dissolving the nucleic acid in the buffer solution for 30 minutes to 1 hour with stirring at 40-70° C., to prepare a nucleic acid stock solution; ii) dissolving chitosan in an acidic buffer solution to prepare a chitosan stock solution; iii) mixing the nucleic acid stock solution in step i) and the chitosan stock solution in step ii) such that the weight ratio of the nucleic acid and the chitosan is 1:1 to 3000:1, followed by stirring at 40-70° C. for 30 minutes to 1 hour; and iv) lowering the temperature of the nucleic acid-chitosan mixture liquid in step iii) to room temperature with stirring.

The buffer solution usable in the preparation of the nucleic acid stock solution may be sodium phosphate dibasic dodecahydrate, sodium chloride, magnesium chloride, potassium chloride, phosphate buffer saline, or N-(2-hydroxyethyl)-piperazine-N'-2-ethanesulfonic acid (HEPES) buffer solution, preferably, sodium phosphate dibasic dodecahydrate, and most preferably 5-300 mM sodium phosphate dibasic dodecahydrate, but is not limited thereto.

The acidic buffer solution usable in the preparation of the chitosan stock solution may be acetic acid, hydrochloric acid, ascorbic acid, lactic acid, nitric acid, glutamic acid, or formic acid, preferably acetic acid, and most preferably 10-300 mM acetic acid, but is not limited thereto.

The composition containing a nucleic acid and chitosan for intra-articular injection may be a thermo-sensitive hydrogel, of which a sol-gel transition occurs depending on the temperature.

The thermo-sensitive hydrogel refers to a hydrogel, of which a phase transition occurs from a sol into a gel or a gel into a sol depending on the temperature. The transition of a sol into a gel is referred to as gelation. The gelation in the present invention is defined as a state in which a polymer having viscoelasticity forms a three-dimensional network structure with increasing temperature, and thus remains without being dissolved in a solvent.

The composition for intra-articular injection having properties of a thermo-sensitive hydrogel is injected into an articular cavity to have viscoelasticity restored by the body temperature, and as a result, the composition is gelated, and thus the degradation rate of the composition is delayed and the retention time of the composition is increased in the articular cavity, thereby protecting an articulation and promoting a restoring effect of damaged cartilage tissues through continuous lubricating and shock absorbing actions.

The composition containing a nucleic acid and chitosan for intra-articular injection is maintained in a homogeneous state and has high stability without layer separation, and the nucleic acid and the chitosan may have a weight ratio of 1:1 to 3000:1. The weight ratio thereof is preferably 10:1 to 300:1, and most preferably 10:1 to 100:1.

The content of the nucleic acid may be 0.1-3 wt %, and preferably 1-2 wt %, relative to a total weight of the composition.

The nucleic acid may have a molecular weight of 10-100,000 kDa, preferably 10-10,000 kDa, and most preferably 50-3,500 kDa. A nucleic acid having a molecular weight of less than 10 kDa makes it impossible to control the degradation rate of the gel, and a nucleic acid having a molecular weight of more than 100,000 kDa makes it difficult to control the viscosity of the gel, and thus the use of the composition is problematic.

The nucleic acid may be deoxyribonucleic acid (DNA), ribonucleic acid (RNA), or a mixture thereof, and preferably deoxyribonucleic acid.

In addition, the deoxyribonucleic acid may include oligonucleotides, polynucleotides, and polydeoxyribonucleotides.

In addition, the content of the chitosan may be 0.001-0.1 wt %, preferably 0.01-0.1 wt % relative to a total weight of the composition.

The molecular weight of the chitosan is preferably 3-1,000 kDa, but is not limited thereto.

The mixing of the nucleic acid and the chitosan is conducted such that the weight ratio of the nucleic acid and the chitosan is 1:1 to 3000:1. Here, it is preferable that the content of the nucleic acid is 0.1-3 wt % relative to a total weight of the composition and the content of the chitosan is 0.001-0.1 wt % relative to a total weight of the composition.

The composition containing a nucleic acid and chitosan for intra-articular injection may contain a water-soluble polymer as an additional ingredient.

The water-soluble polymer may be added to control the degradation rate of the composition containing a nucleic acid and chitosan for intra-articular injection and ensure a lubricating action and therapeutic effects thereof.

The water-soluble polymer is one that can be dissolved or degraded in vivo, and examples thereof may include: polysaccharides, such as hyaluronic acid, chondroitin sulfate, glycogen, dextrin, dextran, dextran sulfate, hydroxypropyl methylcellulose, alginic acid, chitin, and pullulan; proteins, such as collagen, gelatin, and hydrolysates thereof; and synthetic polymer compounds, such as polyvinyl alcohol, polyvinylpyrrolidone, polyacrylic acid, and carboxyvinyl polymers, and a preferable example thereof is hyaluronic acid.

The composition containing a nucleic acid and chitosan for intra-articular injection, which contains the water-soluble polymer as an additional additive, may be one in which nucleic acid, chitosan, and a water-soluble polymer is mixed at a weight ratio of 1-3000:1:1-3000. The weight ratio thereof is preferably 10-1,000:1:10-1,000 and more preferably 25-100:1:25-100.

The hyaluronic acid include a linear or cross-linked form, and the molecular weight thereof may be 20-10,000 kDa, and preferably 500-3,000 kDa, but is not limited thereto.

The composition containing a nucleic acid and chitosan for intra-articular injection can mitigate pain in an articular cavity, reduce inflammation, and induce cartilage regeneration through intra-articular injection thereof.

The composition containing a nucleic acid and chitosan for intra-articular injection may be administered for at least one symptom selected from the group consisting of herniated nucleus pulposus, frozen shoulder, impingement syndrome, carpal tunnel syndrome, degenerative arthritis, tennis/golf elbow, complex regional pain syndrome, other tendinitis symptoms, and chronic articular rheumatism.

Advantageous Effects

The present invention is directed to a composition containing a nucleic acid and chitosan for intra-articular injection. More specifically, it was verified that a composition for intra-articular injection prepared by mixing a nucleic acid and chitosan is biocompatible and allows a sol-gel transition occurring depending on the temperature. Furthermore, it was verified that the injection of the composition of the present invention increases proteoglycan biosynthesis to attain the restoration of cartilage tissues, leading to a reduction in pain, thereby improving a walking speed and a stride length involved in articular movement.

Therefore, it is expected that the composition for intra-articular injection of the present invention is injectable into articular cavities in need of pain relief and therapy and the gelation of the composition injected in the articular cavity lowers the degradation of the composition and increases the retention time of drugs, thereby sufficiently exhibiting a restorative effect of cartilage tissues in the articular cavity through continuous lubricating and shock absorbing actions, leading to excellent therapeutic effects.

BEST MODE FOR CARRYING OUT THE INVENTION

Figure 1:
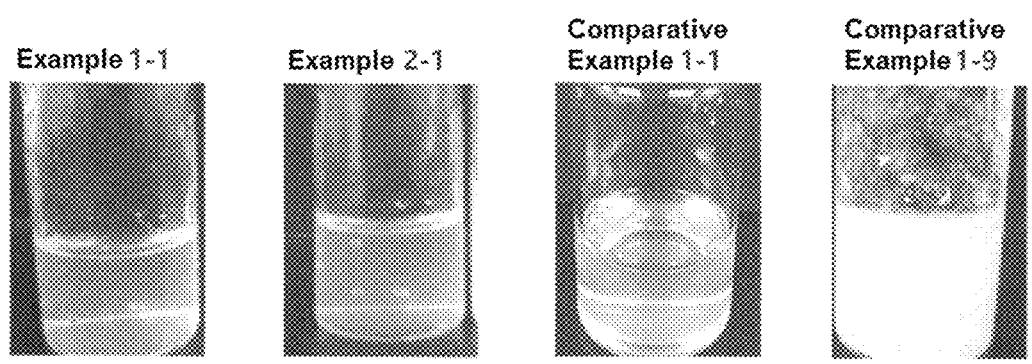
FIG. 1 illustrates the results confirming physical conditions of the compositions for intra-articular injection of the present invention. Each composition for intra-articular injection was prepared, and then left for three days, and thereafter, the transparency, precipitate formation, and layer separation of the composition were investigated.

Hereinafter, preferable embodiments of the present invention will be described in detail. However, the present invention is not limited to the embodiments described herein but may be embodied in other forms. Rather, these embodiments are provided so that this disclosure will be thorough and complete, and will fully convey the scope of the invention to those skilled in the art.

Example 1: Preparation of Compositions Containing Nucleic Acid and Chitosan for Intra-Articular Injection A nucleic acid stock solution was prepared by placing a nucleic acid in a 190 mM sodium phosphate dibasic dodecahydrate buffer solution and dissolving the nucleic acid therein for 30 minutes or more by using a heat stirrer at 70° C.

A chitosan stock solution was prepared by using 100 mM acetic acid.

The prepared nucleic acid and chitosan stock solutions were mixed, and then stirred in a heat stirrer at 70° C. for 30 minutes. Thereafter, the temperature was lowered to room temperature, and the stirring was conducted for 1 hour, thereby preparing each composition containing a nucleic acid and chitosan for intra-articular injection. Here, the mixing was conducted such that the concentrations of the nucleic acid and chitosan were the same as those shown in Table 1 below.

TABLE 1

| Constitution | Final concentration (wt %) | | Mixing ratio (weight ratio) | |
|---|---|---|---|---|
| | Nucleic acid | Chitosan | Nucleic acid | Chitosan |
| Example 1-1 | 1.5 | 0.015 | 100 | 1 |
| Example 1-2 | 0.1 | 0.001 | 100 | 1 |
| Example 1-3 | 0.1 | 0.1 | 1 | 1 |
| Example 1-4 | 3 | 0.001 | 3000 | 1 |
| Example 1-5 | 3 | 0.1 | 30 | 1 |

Example 2: Preparation of Compositions Containing Nucleic Acid, Chitosan, and Hyaluronic Acid for Intra-Articular Injection A nucleic acid stock solution was prepared by placing a nucleic acid in a 190 mM sodium phosphate dibasic dodecahydrate buffer solution and dissolving the nucleic acid therein for 30 minutes or more by using a heat stirrer at 70° C.

A chitosan stock solution was prepared by using 100 mM acetic acid.

The prepared nucleic acid and chitosan stock solutions were mixed, and then stirred in a heat stirrer at 70° C. for 30 minutes. A hyaluronic acid raw material was additionally mixed with the nucleic acid and chitosan mixture solution, and the resultant mixture was stirred in a heat stirrer at 60° C. for 1 hour, and then stirred at room temperature for 3 hours, thereby preparing each composition containing a nucleic acid, chitosan, and hyaluronic acid for intra-articular injection. Here, the mixing was conducted such that the concentrations of the nucleic acid, chitosan, and hyaluronic acid were the same as those shown in Table 2 below.

TABLE 2

| Constitution | Final concentration (wt %) | | | Mixing ratio (weight ratio) | | |
|---|---|---|---|---|---|---|
| | Nucleic acid | Chitosan | Hyaluronic acid | Nucleic acid | Chitosan | Hyaluronic acid |
| Example 2-1 | 1.5 | 0.03 | 1.5 | 50 | 1 | 50 |
| Example 2-2 | 0.1 | 0.001 | 0.1 | 100 | 1 | 100 |
| Example 2-3 | 0.1 | 0.001 | 3 | 100 | 1 | 3000 |
| Example 2-4 | 0.1 | 0.1 | 0.1 | 1 | 1 | 1 |
| Example 2-5 | 0.1 | 0.1 | 3 | 1 | 1 | 30 |
| Example 2-6 | 3 | 0.001 | 0.1 | 3000 | 1 | 100 |
| Example 2-7 | 3 | 0.001 | 3 | 3000 | 1 | 3000 |
| Example 2-8 | 3 | 0.1 | 0.1 | 30 | 1 | 1 |
| Example 2-9 | 3 | 0.1 | 3 | 30 | 1 | 30 |

As the hyaluronic acid, a hyaluronic acid having a molecular weight of 1,000 kDa was used, but a hyaluronic acid having a molecular weight of 20-10,000 kDa may be used.

Comparative Example 1: Preparation of Compositions for Intra-Articular Injection as Comparisons Compositions for intra-articular injection as comparisons were prepared according to mixing ratios corresponding to ingredients and contents shown in Table 3 below. The same preparation methods as in Examples 1 and 2 were used.

TABLE 3

| Constitution | Final concentration (wt %) | | | Mixing ratio (weight ratio) | | |
|---|---|---|---|---|---|---|
| | Nucleic acid | Chitosan | Hyaluronic acid | Nucleic acid | Chitosan | Hyaluronic acid |
| Comparative Example 1-1 | 2 | 0 | 0 | 1 | 0 | 0 |
| Comparative Example 1-2 | 0 | 1 | 0 | 0 | 1 | 0 |
| Comparative Example 1-3 | 0 | 0 | 2 | 0 | 0 | 1 |
| Comparative Example 1-4 | 1.5 | 0 | 1.5 | 1 | 0 | 1 |
| Comparative Example 1-5 | 1.5 | 0.0001 | 0 | 15000 | 1 | 0 |
| Comparative Example 1-6 | 1.5 | 1 | 0 | 1.5 | 1 | 0 |
| Comparative Example 1-7 | 0.001 | 0.0001 | 0.001 | 10 | 1 | 10 |
| Comparative Example 1-8 | 0.001 | 0.000001 | 0.001 | 1000 | 1 | 1000 |
| Comparative Example 1-9 | 1.5 | 0.5 | 1.5 | 3 | 1 | 3 |
| Comparative Example 1-10 | 1.5 | 0.00075 | 1.5 | 2000 | 1 | 2000 |
| Comparative Example 1-11 | 6 | 0.03 | 1.5 | 200 | 1 | 50 |
| Comparative Example 1-12 | 6 | 0.03 | 6 | 200 | 1 | 200 |
| Comparative Example 1-13 | 0 | 0.03 | 1.5 | 0 | 1 | 50 |
| Comparative Example 1-14 | 0 | 0.03 | 6 | 0 | 1 | 200 |

Test Example 1: Verification on Physical Properties of Compositions for Intra-Articular Injection The compositions for intra-articular injection of Example 1 (Examples 1-1 to 1-5), Example 2 (Examples 2-1 to 2-9), and Comparative Example 1 (Comparative Examples 1-1 to 1-14) were used to investigate gelation, gel stability, and gel solubility.

Each composition was subjected to mixing, and then left for 3 days. The transparency and gelation state thereof were observed to the naked eyes. The gelation was investigated by an increase change in viscoelasticity using a rheometer while the temperature was raised from 24° C. to 40° C. by 1° C. and maintained for 1 minute. The gel stability was investigated by precipitate formation and layer separation. For gel solubility, the compositions for intra-articular injection of Example 1, Example 2, Comparative Example 1, were dropped in an aqueous solution at 37.5° C., followed by gelation, and then gel dissolution was investigated while stirring was conducted at 400 rpm for 5 minutes with the temperature maintained at 37.5° C. The results are shown in Table 4 and FIG. 1.

TABLE 4

| | Results after 3 days | | | Results of stirring at 37.5° C. for 5 minutes |
|---|---|---|---|---|
| Constitution | Viscoelasticity | Precipitate formation | Layer separation | Gel dissolution |
| Example 1-1 | ○ | x | x | x |
| Example 1-2 | ○ | x | x | x |
| Example 1-3 | ○ | x | x | x |
| Example 1-4 | ○ | x | x | x |
| Example 1-5 | ○ | x | x | x |
| Example 2-1 | ○ | x | x | x |
| Example 2-2 | ○ | x | x | x |
| Example 2-3 | ○ | x | x | x |
| Example 2-4 | ○ | x | x | x |
| Example 2-5 | ○ | x | x | x |
| Example 2-6 | ○ | x | x | x |
| Example 2-7 | ○ | x | x | x |
| Example 2-8 | ○ | x | x | x |
| Example 2-9 | ○ | x | x | x |
| Comparative Example 1-1 | ○ | x | x | ○ |
| Comparative Example 1-2 | x | x | x | ○ |
| Comparative Example 1-3 | ○ | ○ | ○ | ○ |
| Comparative Example 1-4 | ○ | x | x | ○ |
| Comparative Example 1-5 | ○ | x | x | ○ |
| Comparative Example 1-6 | x | ○ | x | ○ |
| Comparative Example 1-7 | x | x | x | ○ |
| Comparative Example 1-8 | x | x | x | ○ |
| Comparative Example 1-9 | ○ | ○ | x | ○ |
| Comparative Example 1-10 | ○ | x | x | ○ |
| Comparative Example 1-11 | x | ○ | x | x |
| Comparative Example 1-12 | x | ○ | x | x |
| Comparative Example 1-13 | ○ | ○ | ○ | ○ |
| Comparative Example 1-14 | ○ | ○ | ○ | ○ |

Referring to Table 1 and FIG. 1, as for the compositions for intra-articular injection of Example 1 and Example 2, it can be seen that precipitate formation and layer separation did not occur while viscoelasticity was maintained, even after three days, and in terms of gel solubility, gels were formed at 37.5° C. and the formed gels were continuously maintained.

However, as for the compositions for intra-articular injection as comparisons of Comparative Example 1, it was confirmed that precipitate formation or layer separation occurred or lumps were partially formed, making it impossible to measure viscoelasticity, and in terms of gel solubility, gels did not occur at 37.5° C. and even there was gelation, gels were entirely dissolved within 5 minutes. Especially the compositions containing no nucleic acid as in Comparative Examples 1-13 and 1-14, it was confirmed that the compositions have viscoelasticity but precipitate formation and layer separation occurred therein, and gels were formed at 37.5° C. and then were entirely dissolved within 5 minutes, indicating poor stability (see Table 4).

Through these results, it can be seen that the composition for intra-articular injection of the present invention shows thermo-sensitivity depending on the temperature change and continuously maintained a form of a gel even after gelation. Therefore, it can be predicted that the injected composition of the present invention is gelated to have restored viscosity and elasticity in articular cavities, enabling continuous lubricating and shock absorbing actions, thereby protecting articulation and promoting a restorative effect of damaged cartilage tissues through increased drug retention, leading to excellent therapeutic effects for arthritis.

Test Example 2: Verification on Sol-Gel Transition Depending on Temperature

It was verified that hydrogels having sol-gel transition depending on temperature were formed in the compositions for intra-articular injection of Example 1, Example 2, and Comparative Example 1.

A rheometer was used to investigate sol-gel transition. The measurement conditions used here were PU20, gap of 0.5 mm, 0.1 Hz, and 1% stress-strain. The changes of G' (elasticity) and G" (viscosity) were measured while the temperature was raised from 24° C. to 40° C. by 1° C. and maintained for 1 minute. In addition, the sol-gel transition after and before 36° C. was observed to the naked eyes while the temperature of each composition was raised, and the results are shown in FIG. 2.

Figure 2:
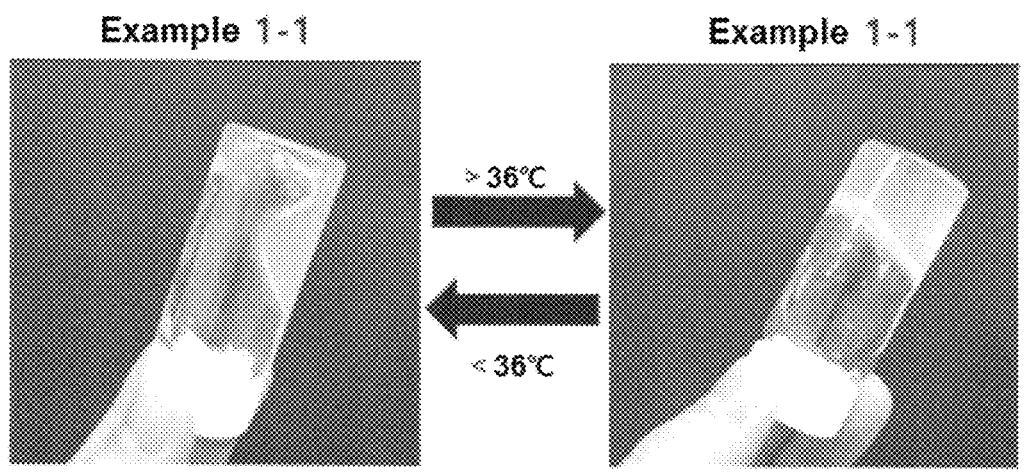
FIG. 2 shows the results confirming the formation of a hydrogel, of which a sol-gel transition occurs depending on the temperature, of the composition for intra-articular injection of Example 1-1 of the present invention.

As shown in FIG. 2, it was observed that the composition for intra-articular injection of Example 1-1 showed a sol form at a temperature of lower than 36° C. whereas was gelated at a temperature exceeding 36° C. It was confirmed that these results were the same in all of the compositions for intra-articular injection of Example 1 and Example 2.

It can be therefore seen that the compositions for intra-articular injection of the present invention exhibit a property as a thermo-sensitive hydrogel of which a sol-gel transition occurs depending on the temperature.

Test Example 3: Preparation of Experimental Animals

For the animal experiment, 7-week-old Sprague-Dawley male rats were purchased from Young Bio (Seongnam, Korea). A solid feed for experimental animals (Harlan laboratories, Inc., USA) was used as a feed. The solid feed was placed in a feeder and was freely available. For drinking water, tap water was filtered through a filter sterilizer, and irradiated with ultraviolet light, and then freely available through an automatic water supply device. The environment of an experimental animal breeding room was maintained at a temperature of 23±3° C., relative humidity of 55±15%, lighting time of 12 hours (8:00 am to 8:00 pm), and illumination of 150-300 Lux.

Test Example 4: Verification on Biocompatibility of Compositions for Intra-Articular Injection The rats in Test Example 3 were breathing anesthetized using isoflurane. The hairs on the right knee of the anesthetized rats were shaved, and a site of injection was disinfected by betadine cotton, and then 0.05 cc of the compositions for intra-articular injection of Example 1-1 and Example 1-2 were injected into the right knee by using 1 cc-sterilized insulin syringe and a 30-gauge needle. Also, saline as a control group was injected by the same method.

After the injection of the composition for intra-articular injection, the rats were sacrificed with $CO_2$ gas, and then the right knee tissue was cut, and fixed with formalin, and embedded in paraffin through a series of dehydration processes, thereby manufacturing a paraffin block. Here, the left knee tissue of non-treated rates as a normal group was also used to manufacture a paraffin block. Each of the paraffin blocks was sliced into a tissue section with 5 μm thickness, and the tissue section was reacted with Mayer's hematoxyline (Sigma, USA) solution for 1 second, and then washed with flowing water for 10 minutes. Thereafter, the tissue section was reacted with eosin (Sigma, USA) solution for 3 seconds. The stain-completed tissue section was dehydrated, and then sealed using Permount® (Fischer Scientific, USA). Biocompatibility of the composition was investigated by observing the presence or absence of histopathological changes using a microscope on the H&E stained tissue section. The results are shown in FIG. 3.

Figure 3:
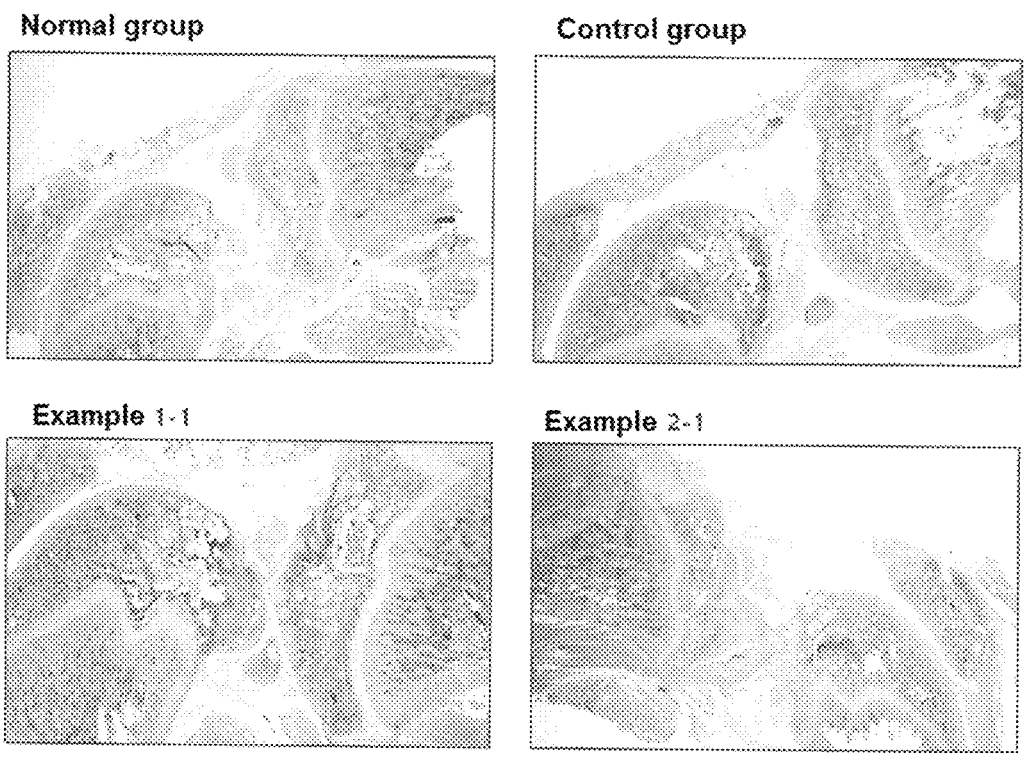
FIG. 3 shows the results confirming biocompatibility through the presence or absence of an inflammation reaction by the administration of the compositions for intra-articular injection.

Referring to the H&E stained tissue sections shown in FIG. 3, an inflammation response was not observed in the injection of the compositions for intra-articular injection of Example 1-1 and Example 2-1 like the control group injected with saline and the non-treated normal group.

Therefore, it was verified that the compositions for intra-articular injection of the present invention is a biocompatible composition causing neither immune response nor inflammation response.

Test Example 5: Verification on Pain Relieving Effect of Compositions for Intra-Articular Injection The rats in Test Example 3 were breathing anesthetized using isoflurane. The hairs on the right knee of the anesthetized rats were shaved, and a site of injection was disinfected by betadine cotton, and then 1 mg/50 μL monosodium iodoacetate (MIA) diluted in 0.9% sodium chloride (NaCl) was once injected into the knee through intra-articular injection using a 1 cc-sterilized insulin syringe and a 30-gauge needle, and then the rats were bred for 1 week, thereby causing arthritis.

The arthritis-induced rats were breathing anesthetized using isoflurane. The hairs on the right knee of the anesthetized rats were shaved, and a site of injection was disinfected by betadine cotton, and then the compositions for intra-articular injection of Example 1, Example 2, and Comparative Example 1 were injected once a week for a total of four times by using 1 cc-sterilized insulin syringe and a 30-gauge needle. The composition was injected in 0.05 cc each time. Here, saline was injected into the right knee as a control group, and rats without arthritis induction were used as a normal group.

The pain relieving effect was investigated by injecting the composition for intra-articular injection into the rats four times, photographing the bottom surface of a plastic cage (150 cm×13 cm×16 cm) through a video camera when the rat passed through the plastic cage to observe the movement of the rat, and then analyzing the walking speed and stride length of the rat using the photographed images through a program recognizing foot soles of the rat. The results are shown in FIG. 4.

Figure 4:
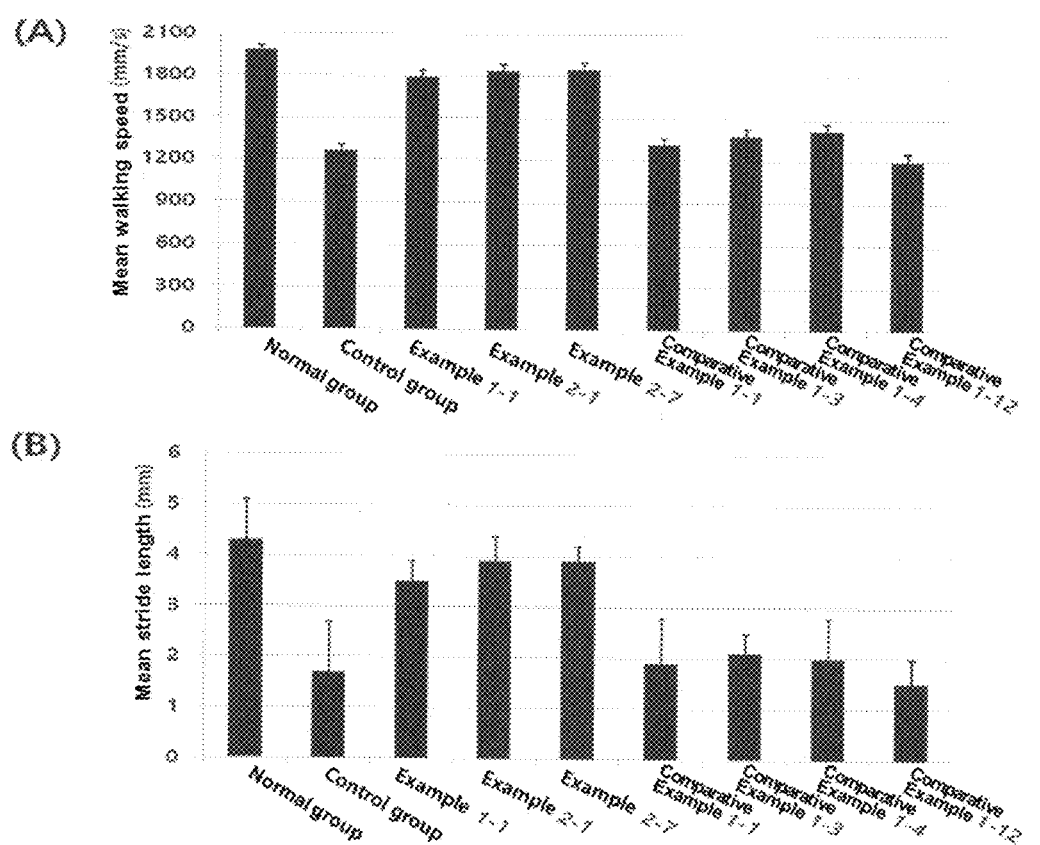
FIG. 4 shows the results confirming the walking speed (FIG. 4A) and stride length (FIG. 4B) of rats by the injection of the compositions for intra-articular injection (of Example 1-1, Example 2-1, and Example 2-7) of the present invention after arthritis induction.

As shown in the results confirming the walking speed (FIG. 4A) and stride length (FIG. 4B) of the rats in FIG. 4, the walking speed and stride length of rats were reduced in the control group injected with saline compared with the normal group, whereas the walking speed and stride length reduced due to arthritis were restored to be similar to those of the normal group when the compositions for intra-articular injection of Example 1-1, Example 2-1, and Example 2-7 were injected. Similar results thereto were confirmed in all of the compositions for intra-articular injection of Example 1 and Example 2. However, the walking speed and stride length of rats in the compositions of Comparative Example 1 including the compositions for intra-articular injection of Comparative Example 1-1, Comparative Example 1-3, Comparative Example 1-4, and Comparative Example 1-12, shown in FIG. 4, were similar to those in the control group injected with saline.

The reason is thought that arthritis was treated by the compositions for intra-articular injection of the present invention injected into articular cavities, so that the pain by arthritis was relieved and thus the walking speed and stride length of the rats were increased. In addition, it is predicted that the composition for intra-articular injection of the present invention has thermo-sensitivity, and has viscoelasticity due to the gelation by the body temperature, thereby reducing a friction between an upper bone and a lower bone in the articulation and absorbing shock, leading to an increase in the pain relieving effect.

Test Example 6: Verification on Cartilage Regeneration Effect of Composition for Intra-Articular Injection Test Example 6-1: Establishment of Arthritis Animal Models and Injection of Compositions The rats in Test Example 3 were breathing anesthetized using isoflurane. The hairs on the right knee of the anesthetized rats were shaved, and a site of injection was disinfected by betadine cotton, and then 1 mg/50 μL monosodium iodoacetate (MIA) diluted in 0.9% sodium chloride (NaCl) was once injected into the knee through intra-articular injection using a 1 cc-sterilized insulin syringe and a 30-gauge needle, and then the rats were bred for 1 week, thereby causing arthritis. The successful induction of arthritis was confirmed by reductions in the walking speed and stride length of the rats.

The right knee of the arthritis-induced rates was injected with the compositions for intra-articular injection of Example 1, Example 2, and Comparative Example 1 and saline as a control group, and then the rats were placed in a cage, and then bred in a stable environment. Here, the compositions for intra-articular injection and saline were injected by 0.05 cc once a week for a total of four times.

Test Example 6-2: Verification on Cartilage Regeneration Effect of Composition for Intra-Articular Injection After the composition for intra-articular injection of the present invention was injected four times as shown in Test Example 6-1, the rats were sacrificed by $CO_2$ gas, and then both knee cartilage tissues were cut from the non-treated left knee (normal group) and the right knees injected with respective compositions of the examples and the comparative examples, followed by investigation of the cartilage regeneration effect.

The cartilage regeneration effect was investigated through proteoglycan staining. Proteoglycans are substances involved in the proliferation of chondroblasts, and the proliferation of chondroblasts is one of the essential procedures for cartilage generation.

The knee cartilage tissue was fixed with formalin, and embedded in paraffin through a series of dehydration processes, thereby manufacturing a paraffin block. The manufactured paraffin block was sliced into a tissue section with 5 μm thickness, and the proteoglycans were stained by Safranin O staining to compare the amount of proteoglycans. Here, the left knee tissue of the rats without arthritis induction was used as a normal group, and the knee tissue of the rats subjected to arthritis induction and then saline treatment was used as a control group. The amount of proteoglycans was calculated as a relative staining area ratio based on the amount of proteoglycans in the normal group as 100%. The results are shown in FIG. 5 and Table 5.

TABLE 5

| Constitution | Proteoglycan (%) |
| --- | --- |
| Normal group | 100 |
| Control group | 42 |
| Example 1-1 | 83 |
| Example 1-3 | 81 |
| Example 1-4 | 84 |
| Example 2-1 | 88 |
| Comparative Example 1-1 | 59 |
| Comparative Example 1-2 | 47 |
| Comparative Example 1-5 | 60 |
| Comparative Example 1-10 | 62 |

Figure 5:
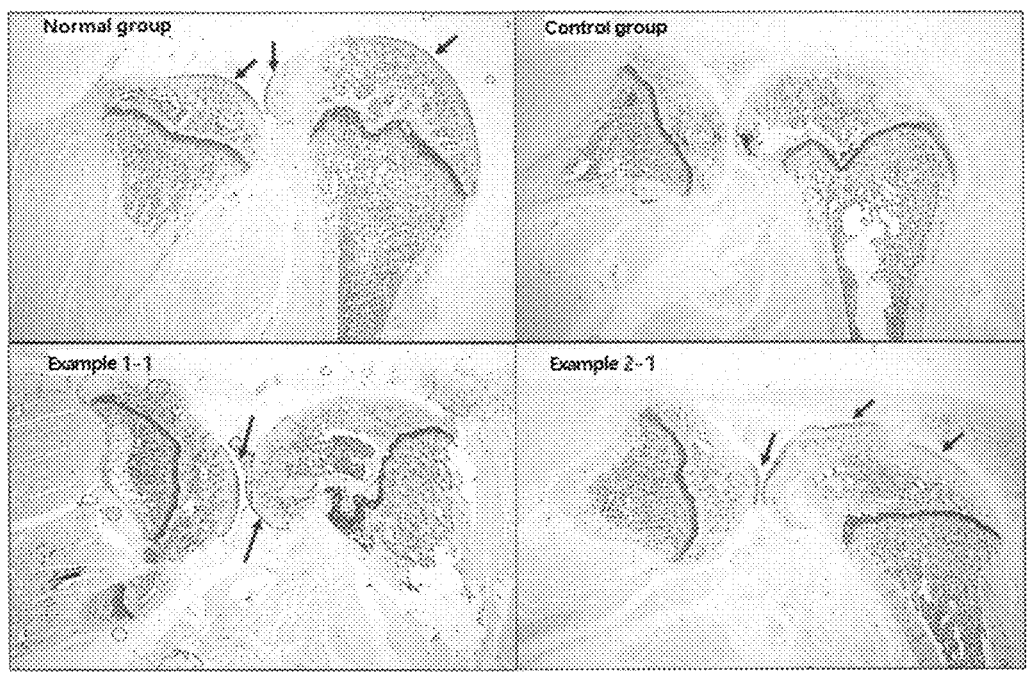
FIG. 5 shows the results confirming the biosynthesis extent of proteoglycans by the injection of the compositions for intra-articular injection (of Example 1-1 and Example 2-1) of the present invention after arthritis induction.

As shown in FIG. 5, with respect to proteoglycans on the cartilage surface red stained with Safranin O (indicated by arrows), it can be see that the red stain area on the cartilage surface was reduced in the control group compared with the normal group, indicating that the amount of proteoglycans was reduced by arthritis induction. Whereas, it was verified that the amount of proteoglycans on the cartilage surface was increased and thus a red stain area was increased, in the injection of the compositions for intra-articular injection of Example 1-1 and Example 2-1 compared with the control group.

According to the results of calculating relative stain area proportion of proteoglycans in Table 5, the control group showed a numerical value of 42% compared with the normal group, whereas the injection of the compositions for intra-articular injection of Example 1-1, Example 1-3, Example 1-4, and Example 2-1 showed a numerical value of 80% or more. However, it can be seen that the injection of the compositions for intra-articular injection of Comparative Example 1-1, Comparative Example 1-2, Comparative Example 1-5, and Comparative Example 1-10 showed lower numerical values compared with the injection of the compositions for intra-articular injection of Example 1 and Example 2. Therefore, it can be seen that in cartilage in the articulation cavity with arthritis induction by the intra-articular injection of the compositions for intra-injection of Example 1 and Example 2, the expression of proteoglycans was increased and thus cartilage regeneration and restoration occurred.

The invention claimed is:

1. A composition for intra-articular injection, the composition comprising a nucleic acid and chitosan,
   wherein the content of the nucleic acid is 0.1-3 wt % relative to a total weight of the composition,
   wherein the content of the chitosan is 0.001-0.1 wt % relative to a total weight of the composition, and
   wherein the weight ratio of the nucleic acid and the chitosan is 1:1 to 3000:1.

2. The composition of claim 1, wherein the content of the nucleic acid is 1-2 wt % relative to a total weight of the composition.

3. The composition of claim 1, wherein the content of the chitosan is 0.01-0.1 wt % relative to a total weight of the composition.

4. The composition of claim 1, wherein the weight ratio of the nucleic acid and the chitosan is 10:1 to 300:1.

5. The composition of claim 1, wherein the nucleic acid is deoxyribonucleic acid (DNA), ribonucleic acid (RNA), or a mixture thereof.

6. The composition of claim 5, wherein the nucleic acid is deoxyribonucleic acid (DNA).

7. The composition of claim 6, wherein the deoxyribonucleic acid is selected from oligonucleotides, polynucleotides, and polydeoxyribonucleotides.

8. The composition of claim 1, wherein the nucleic acid has a molecular weight of 1-100,000 kDa.

9. The composition of claim 8, wherein the nucleic acid has a molecular weight of 10-10,000 kDa.

10. The composition of claim 9, wherein the nucleic acid has a molecular weight of 50-3,500 kDa.

11. The composition of claim 1, wherein the chitosan has a molecular weight of 3-1,000 kDa.

12. The composition of claim 1, wherein the composition contains a water-soluble polymer as an additional ingredient.

13. The composition of claim 12, wherein the water-soluble polymer is at least one selected from the group consisting of hyaluronic acid, chondroitin sulfate, glycogen, dextrin, dextran, dextran sulfate, hydroxypropyl methylcellulose, alginic acid, chitin, pullulan, collagen, gelatin, hydrolysates of all of the above, polyvinyl alcohol, polyvinylpyrrolidone, polyacrylic acid, and carboxyvinyl polymers.

14. The composition of claim 13, wherein the water-soluble polymer is hyaluronic acid.

15. The composition of claim 1, wherein the composition is a thermo-sensitive hydrogel.

16. The composition of claim 1, wherein the intra-articular injection is an administration for at least one symptom selected from the group consisting of herniated nucleus pulposus, frozen shoulder, impingement syndrome, carpal tunnel syndrome, degenerative arthritis, tennis/golf elbow, complex regional pain syndrome, other tendinitis symptoms, and chronic articular rheumatism.

17. The composition of claim 2, wherein the nucleic acid is deoxyribonucleic acid (DNA), ribonucleic acid (RNA), or a mixture thereof.

18. The composition of claim 2, wherein the nucleic acid has a molecular weight of 1-100,000 kDa.

19. The composition of claim 3, wherein the chitosan has a molecular weight of 3-1,000 kDa.

* * * * *